(12) United States Patent
Rogers et al.

(10) Patent No.: US 9,649,504 B2
(45) Date of Patent: May 16, 2017

(54) IMPLANTABLE CLIPT ILLUMINATION SYSTEM

(71) Applicant: Rogers Sciences, Inc., Beverly, MA (US)

(72) Inventors: Gary S. Rogers, Wenham, MA (US); Samuel L. Hill, Somerville, MA (US)

(73) Assignee: ROGERS SCIENCES, INC., Beverly, MA (US)

( * ) Notice: Subject to any disclaimer, the term of this patent is extended or adjusted under 35 U.S.C. 154(b) by 624 days.

(21) Appl. No.: 14/074,218

(22) Filed: Nov. 7, 2013

(65) Prior Publication Data

US 2014/0128943 A1 May 8, 2014

Related U.S. Application Data

(60) Provisional application No. 61/723,526, filed on Nov. 7, 2012.

(51) Int. Cl.
*A61N 5/06* (2006.01)

(52) U.S. Cl.
CPC ......... *A61N 5/0603* (2013.01); *A61N 5/0601* (2013.01); *A61N 5/062* (2013.01); *A61N 2005/0602* (2013.01); *A61N 2005/063* (2013.01); *A61N 2005/0604* (2013.01); *A61N 2005/0609* (2013.01); *A61N 2005/0659* (2013.01)

(58) Field of Classification Search
CPC ...... A61N 5/06; A61N 5/0601; A61N 5/0603; A61N 5/0604; A61N 5/0609; A61N 5/061; A61N 5/062; A61N 2005/0602; A61N 2005/063; A61N 2005/0632; A61N 2005/0645; A61B 1/06; A61B 6/4057; A61B 6/145
USPC ........ 607/8–92, 96, 100, 133; 606/7, 13–15; 128/898
See application file for complete search history.

(56) References Cited

U.S. PATENT DOCUMENTS

| | | | |
|---|---|---|---|
| 7,122,568 B1 | 10/2006 | Allison et al. | |
| 8,652,187 B2 * | 2/2014 | Wells | A61N 1/36032 607/3 |
| 2002/0087206 A1 | 7/2002 | Hirschberg et al. | |
| 2006/0100679 A1 * | 5/2006 | DiMauro | A61N 5/0601 607/94 |
| 2007/0288071 A1 | 12/2007 | Rogers et al. | |
| 2008/0281305 A1 | 11/2008 | Baynham et al. | |

(Continued)

OTHER PUBLICATIONS

International Search Report and Written Opinion mailed on Feb. 27, 2014, in connection with the corresponding PCT Application No. PCT/US2013/068903.

(Continued)

*Primary Examiner* — Ahmed Farah
(74) *Attorney, Agent, or Firm* — Gesmer Updegrove LLP

(57) ABSTRACT

A light-based therapy device is provided that includes a controller mechanism that produces power and control signals to enable operation of one or more medical devices. An implantable light delivery device (IM-LDD) is coupled to the controller mechanism that receives the power and the control signals to enable a light source to emit sufficient illumination. The light source is implanted within body cavities enabling energy at one or more wavelengths to reach and provide therapy treatment to a selected region.

30 Claims, 11 Drawing Sheets

(56) References Cited

U.S. PATENT DOCUMENTS

| | | | | |
|---|---|---|---|---|
| 2010/0249891 A1* | 9/2010 | O'Flynn | ............. | A61F 2/07 |
| | | | | 607/92 |
| 2010/0292629 A1* | 11/2010 | Dacey, Jr. | ............. | A61L 2/0011 |
| | | | | 604/8 |
| 2011/0125078 A1* | 5/2011 | Denison | ............. | A61N 5/0601 |
| | | | | 604/20 |
| 2011/0295347 A1* | 12/2011 | Wells | ............. | A61N 1/36032 |
| | | | | 607/89 |
| 2012/0303101 A1* | 11/2012 | Rogers | ............. | A61N 5/062 |
| | | | | 607/90 |
| 2015/0032190 A1* | 1/2015 | Acker | ............. | A61N 5/0601 |
| | | | | 607/88 |
| 2015/0246242 A1* | 9/2015 | Delp | ............. | A61N 1/0551 |
| | | | | 604/20 |

OTHER PUBLICATIONS

International Preliminary Report on Patentability issued on May 21, 2015 in connection with corresponding PCT Application No. PCT/US2013/068903.

* cited by examiner

IMPLANTABLE CLIPT ILLUMINATION SYSTEM

PRIORITY INFORMATION

This application claims priority from provisional application Ser. No. 61/723,526 filed Nov. 7, 2012, which is incorporated herein by reference in its entirety.

BACKGROUND OF THE INVENTION

The invention is related to the field of Continuous Low Irradiance Photodynamic Therapy (CLIPT), and in particular to an implantable CLIPT illumination system.

Photodynamic Therapy (PDT) is a two-step, drug-device combination therapy that uses specific wavelengths of light to activate photosensitive drugs to kill cancer cells. Widespread adoption of PDT as a form of cancer treatment has been limited by a number of factors, most notably excessive morbidity, lack of penetration of the energy and the complexity of administering the therapy. CLIPT was introduced as a new therapeutic paradigm to reduce these standard PDT limitations and side-effects by delivering light at ultra-low dose-rates (0.1-0.5 mW) over a period of hours to days compared to traditional PDT delivered at a high dose-rate (2-5 W) occurring over a period of seconds to minutes. In recent clinical studies of 15 patients under a Susan G. Komen for the Cure® Foundation grant (Komen Study) and a NIH SBIR Phase I grant (NIH SBIR Study), CLIPT has shown >80% tumor response, as evidence by tumor shrinkage and or apoptosis at a depth well beyond conventional PDT. The side effects were minimal edema and eccymoses, no necrosis, and no full thickness ulcerations of normal tissues as often occur with standard radiation and conventional PDT.

The CLIPT 2nd Gen (light delivery device) LDD includes the development of the Light Diffusion Technology (LDT) manufacturing process that enables light emission from the LDD surface in a highly controllable, uniform and scalable manner. The 1st Gen LDD utilizing Lumitex's technology was a weaved collection of fiber optic cables that were bent sharply at several locations along the length of the fiber. The bending of the fiber causes light to leak from the fiber illuminating a small portion of a light illumination surface that consists of hundreds to thousands of these bent fibers spread across 7 layers of fiber optic material. This weaved fiber approach provides imprecise quantities of light at the treatment site because the bending (the mechanism of light leakage) of the fiber is not uniform from bend to bend and the location of bending along similarly aligned fibers can be random from fiber to fiber. The 1st Gen LDD exhibited irradiance uniformity performance of −37%/+28% across the 10 cm×10 cm area of the device. Not only is the light uniform inconsistent, the device is heavy, not flexible, has low optical efficiency, and is not scalable to larger areas.

In comparison, the LDT used on the 2nd Gen LDD uses a precision mounted and motorized laser scoring process that can be moved along the length of one or more fibers. The scoring process in general allows for light to exit the fiber by non-total-internal-reflection bending to create precision illumination along the entire length of the fiber based LDD. Irradiance repeatability of 2nd Gen LDD devices is within +/−2%, far below our target goal of +/−10% and far below the irradiance variability of the 1st Gen LDD. With precision laser etching of the fiber, it allows for predictable illumination along the length of one fiber in a linear or non-linear controlled output. Due to the etching process, similarly aligned fibers will have similar etching and performance such that an array of fibers can be stacked in a one-dimension, two-dimensional, or three-dimensional pattern for predictable and uniform illumination. Due to the simpler design and fabrication method, the overall thickness of the LDD pad (the 10 cm$^2$ illumination surface) is 0.7 mm with a maximum working bend radius of 5 cm along the length (longitudinal) of the fiber LDD and 1 cm across (lateral) the LDD. The 1st Gen LDD had a thickness of 10 mm and a longitudinal bend radius of approximately 45 cm and a lateral bend radius of approximately 60 cm, significantly larger than that of the 2nd Gen LDD. In general the LDT process also significantly reduces the amount of fiber optic material required for the LDD, which results in significantly improved device mechanical properties, particularly body contour flexibility, as well as a lower cost to manufacture. Additionally, by utilizing the fiber in a more predictable manner optical efficiency increased from under 10% with the 1st Gen LDD to nearly 15% efficiency with the 2nd Gen LDD.

The second major innovation of the 2nd Gen LDD was the extension of this laser scoring technique to control the irradiance distribution pattern on the LDD surface. It has been demonstrated the ability to use this new manufacturing scoring technique to correct for laser mode patterns and achieve our irradiance uniformity specification. When using a laser source, the mode pattern of the laser beam is Gaussian which means the beam has its greatest intensity on center and the intensity falls off in intensity along the width of the beam with a Gaussian profile. Thus, illumination on the LDD emission surface was brighter in the middle and decreased in brightness towards the edges of the LDD. This was a problem with both the 1st Gen LDD woven architecture and with the new 2nd Gen LDD. Possible means for mode or Gaussian correction include diffusers, mode scrambling via pinching fibers, or moving fibers from the center of the LDD to the edges and some of the fibers from the edges to the center to smooth out the intensity across the LDD surface.

SUMMARY OF THE INVENTION

According to one aspect of the invention, there is provided an implantable light delivery device (IM-LDD). The IM-LDD includes a light source that can emit sufficient illumination and be implanted within body cavities or luminal surfaces enabling energy at one or more wavelengths to reach and provide photodynamic therapy (PDT) treatment at selected region.

According to another aspect of the invention, there is provided a light-based therapy device. The light-based therapy device includes a controller mechanism that produces power and control signals to enable operation of one or more medical devices. An implantable light delivery device (IM-LDD) is coupled to the controller mechanism that receives the power and the control signals to enable a light source to emit sufficient illumination. The light source is implanted within body cavities enabling energy at one or more wavelengths to reach and provide therapy treatment to a selected region.

According to another aspect of the invention, there is provided a method of performing photodynamic therapy. The method includes providing a controller mechanism that produces power and control signals to enable operation of one or more medical devices. Also, the method includes providing an implantable light delivery device (IM-LDD) that is coupled to the controller mechanism that receives the power and the control signals to enable a light source to emit sufficient illumination. Furthermore, the method includes implanting the light source within body cavities enabling energy at one or more wavelengths to reach and provide therapy treatment to a selected region.

DETAILED DESCRIPTION OF THE INVENTION

Figure 1A:
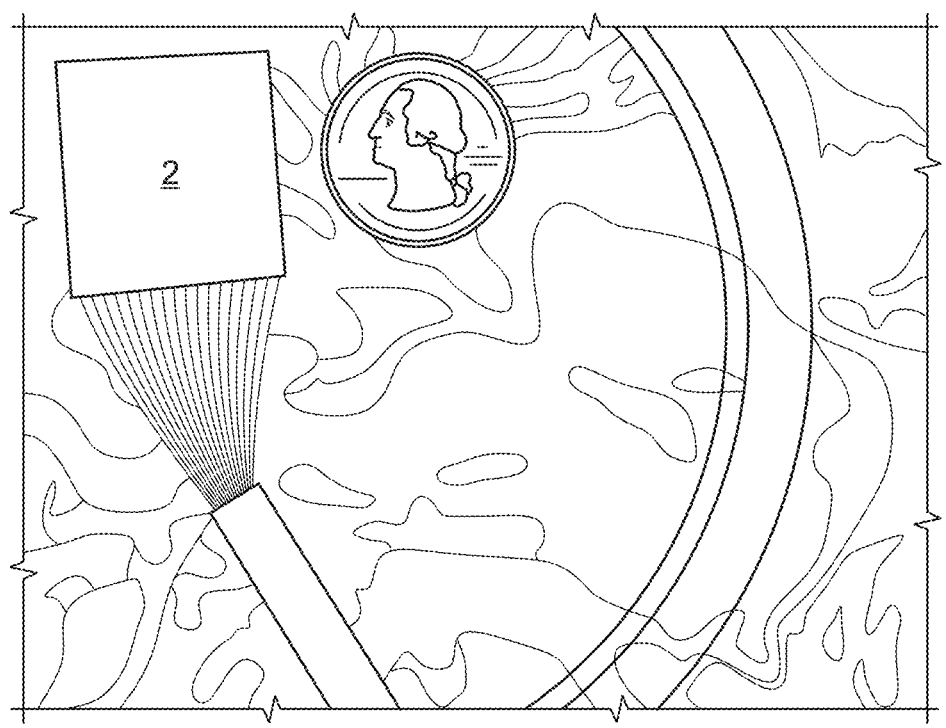
FIGS. 1A-1B are schematic diagrams illustrating the implantable light delivery device (IM-LDD) used in accordance with the invention.

The present invention aims to evolve already established light diffusion developments in CLIPT technology by creating an implantable light delivery device (IM-LDD) that can be inserted for temporary or extended periods into the cavities within the human body and along luminal surfaces, including, but not limited to the esophagus, upper and lower GI tract, genito-urinary tract, bladder, pelvis, peritoneum, pulmonary cavity, hepatobilliary tree, bronchial tree, blood vessels and calvarium/CNS.

The advancement of an IM-LDD will address the unmet need for developing low-morbidity, high-impact therapies for advanced-stage cancers in or around these luminal surfaces and body cavities. The IM-LDD can be used without drugs as an internal illumination and energy source only. Additionally, the IM-LDD could be used in binary therapies with drugs including photosensitizers for use in PDT and CLIPT, chemotherapeutic agents, nanoparticles including polyethylene glycol-coated gold nanorods (PEG-NR) or a combination of drugs to provide energy-drug therapeutic modalities at either high-or-low illumination light levels for periods under 1 second to as long as several days.

The invention is an implantable light delivery device that can emit sufficient illumination and be implanted within body cavities such as the peritoneum or pelvis enabling energy at one or more wavelengths to reach and provide treatment of deep-seated cancer that would otherwise require opening of the body cavity to reach the target tissue. The IM-LDD can be fabricated into multiple rigid and flexible cylindrical shapes to be used on luminal surfaces within the body.

For light-activated therapies, there are several reasons internal illumination is a consideration for various diseases in or adjacent to body cavities and luminal surfaces. Tumor nodules are deep-seated and too far from the body surface for energy delivery from the skin surface. To reach deep seated tumors requires endoscopic or catheter based single point illumination or requires surgery to provide external access to an illumination source. In many cases, surgery and external laser light delivery is the primary mechanism for light delivery to deep-seated tumors.

Given that many cancer therapies require continuous, repeated and recurrent treatments, a repeated surgery is morbid and impractical for both pre-clinical experiments and ultimate human application. Typically, the method of light delivery occurs with high-energy density lasers or glass fiber optic devices which typically present the illumination in a focused region-of-interest (approximately 5-10 mm in diameter). Given this size, it would require a significant amount of time to treat multiple tumor nodules spread over a larger region-of-interest as is seen with many subjects with advanced stage cancers. Frequently, the laser or illumination levels are significantly high to cause tissue damage to the tumor sites and healthy tissue surrounding the tumor sites.

Given the limitations of conventional light-delivery for deep seated cancers in or around cavities and luminal surfaces, the inventive IM-LDD can 1) be implantable to efficiently emit light at depth, 2) emit light over a large (human-scale) region-of-interest (ROI), 3) be implanted for an extended period of time to provide chronic care to patients who may develop recurrence, and 4) provide the ability to deliver either high-irradiance or low-irradiance illumination over varying electromagnetic wavelengths from under 1 second to days.

The IM-LDD has the potential for a range of applications that require light-activated therapies. For example the IM-LDD could be applied for current treatment of pancreatic and ovarian cancer when PDT is applied. For example, PDT has been used with limited success in peritoneal spread of ovarian cancer and is associated with significant morbidity. It entails administration of a light-activated photosensitizer drug to the patient followed by opening the abdominal cavity for the surgeon to administer the light energy to the target site. The photochemical reaction generates free-radicals that destroy the tumor. Due to the high dose-rate of photons administered and lack of high specificity of the drug, bowel necrosis, among other serious adverse events, limit PDT's use. With an IM-LDD there is a possibility to provide repeated, continuous or recurrent light delivery with a single minimally invasive surgery, provide targeted illumination, deliver light at lower-energy to reduce morbidity, potentially provide illumination for months to years, and provide the opportunity for home-based therapy.

Additionally, based upon our pre-clinical studies, a new therapeutic modality that has arisen is using near infrared (NIR) light delivery devices implanted within the peritoneal cavity to activate gold nanoparticles for photothermal therapy in treating advanced-stage ovarian cancer. As therapies with different molecular sizes, chemical compositions, and pharmacokinetics become available for metastatic ovarian cancer, it is anticipated that generalized strategies for improving delivery of these therapies, such as photosensitizers or chemotherapies, to tumors will result in reduced tumor burden, toxicity, morbidity, and mortality rates.

One such strategy for improving transport of these therapeutic agents involves harnessing the unique electromagnetic and optical properties of gold nanoparticles to produce tumor-localized hyperthermia and enhanced permeability of tumor vasculature. Polyethlylene glycol-coated gold-nanorods (PEG-NR) are one such form of gold nanoparticles which offers superior absorption and heating, are relatively non-cytotoxic, and are highly stable. Internal NIR light delivery through an IM-LDD would also benefit this type of light-activated therapy.

Previous studies have shown in mouse models that external NIR light activation of PEG-NRs which accumulate selectively in tumor induced tumor-localized heating that increased cell permeability which enhanced accumulation of the chemotherapeutic agents delivered, prolonging the time to tumor progression and improving survival. Due to several of the issues mentioned regarding external illumination of deep-seated tumors during light-activated therapies, one can create several miniaturized IM-LDDs for a study involving nude-mice implanted with a human-cell-line of ovarian cancer.

FIG. 1A shows a miniaturized 1 $cm^2$ IM-LDD 2 that was developed to be flexible and anatomically contouring and similar to the 10 $cm^2$ developed for the clinical studies of chest wall progression of breast cancer. The miniaturized IM-LDD 2 was composed of a uniquely treated optical element array that could deliver the required therapeutic doses of NIR energy for PEG-NR activation. The IM-LDD 2 was tethered to an 808 nm NIR laser.

The invention can also implement PTT (Photo Thermal Therapy) that can include activation of nanoparticles, in particular, the plasmonic effect irradiation induces on gold nanorods. The implanted device activates nanorods that create pores in the tumor allowing large molecule chemo agents to penetrate. This is somewhat different than PDT where the light activates the drug to emit free-radicals and directly kill tumor cells. The pores could also allow photo-activated drugs to traverse membranes.

Figure 1B:
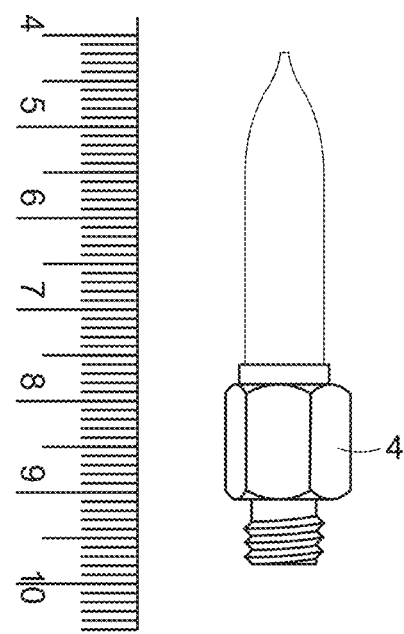
Figure 2A:
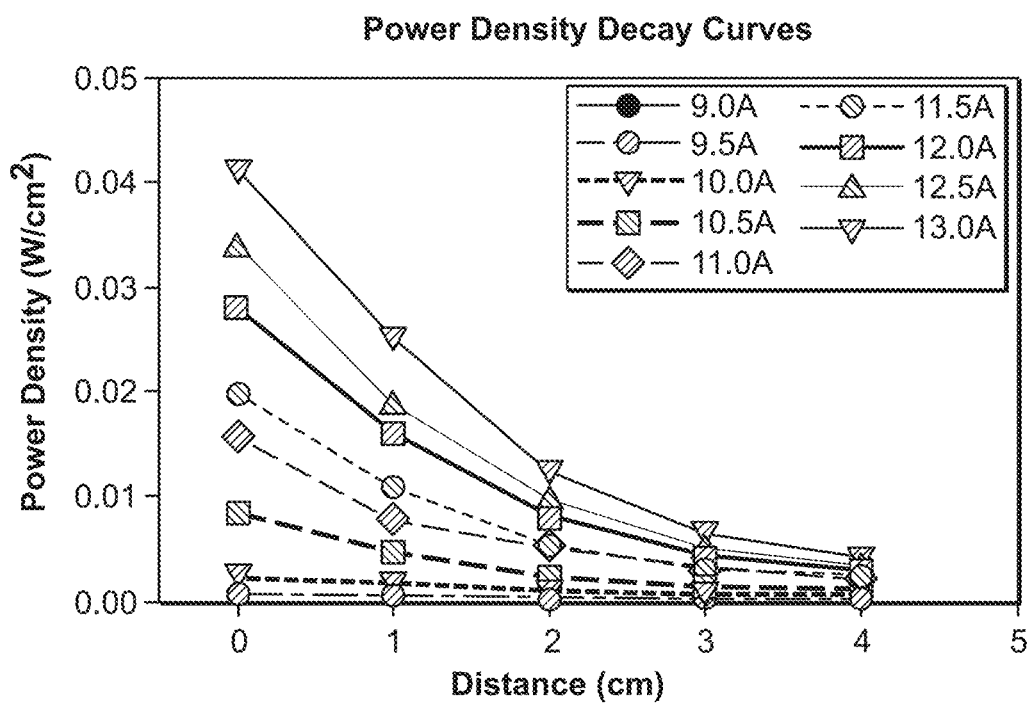
FIGS. 2A-2B are graphs illustrating testing of the IM-LDD prototypes and the illumination profile of the IM-LDD.
Figure 2B:
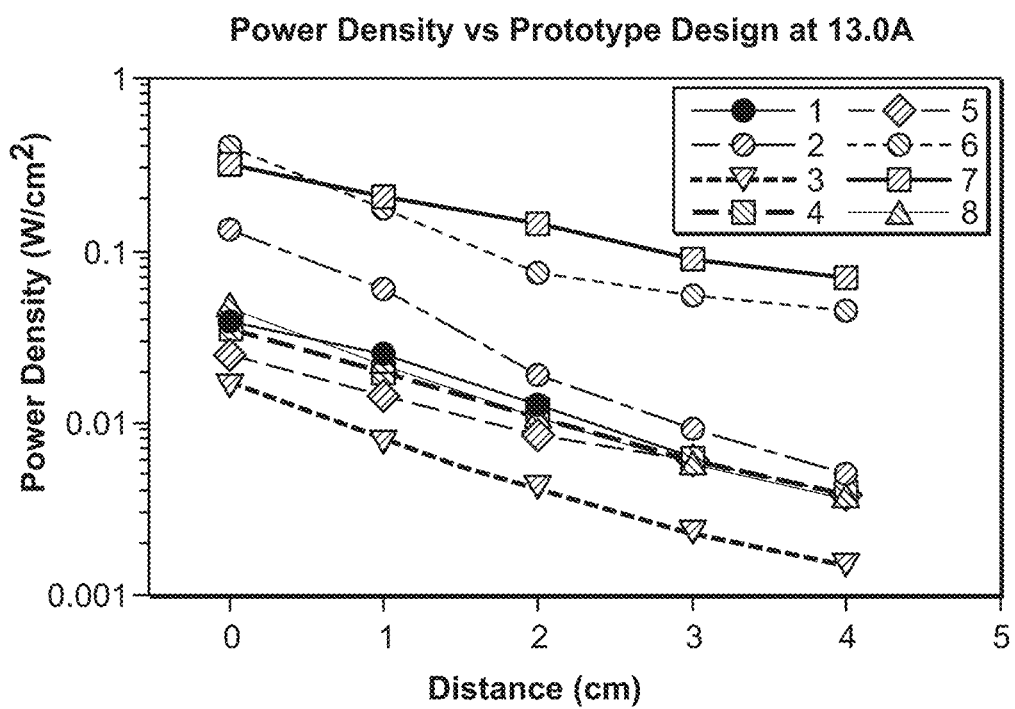

Another early prototype consists of a glass rod 4 that is nearly the length of the mouse peritoneal cavity and provides a highly diffuse 360-degree beam spread along its entire length, as shown in FIG. 1B. Several IM-LDDs were developed and tested to measure output power density as a function of distance, as shown in FIGS. 2A-2B.

Figure 3A:
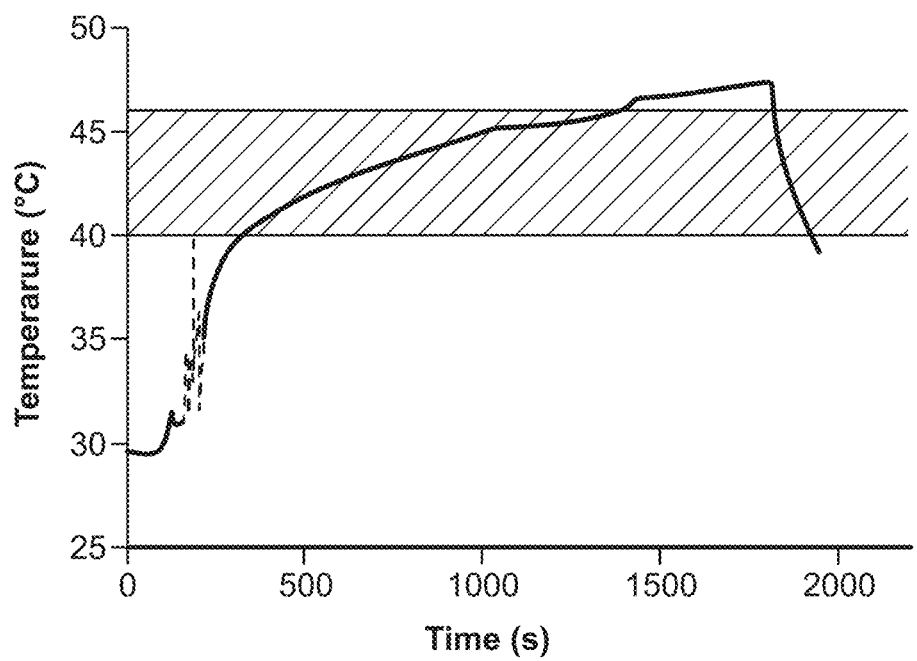
FIGS. 3A-3B are graphs illustrating rapid heating of the IM-LDD to the sub-ablative temperature range to activate PEG-NRs in vivo; and PEG-NRs ("GNR") with NIR treatment increased the accumulation of doxorubicin in human CP70 ovarian tumor cells in a mouse model.
Figure 3B:
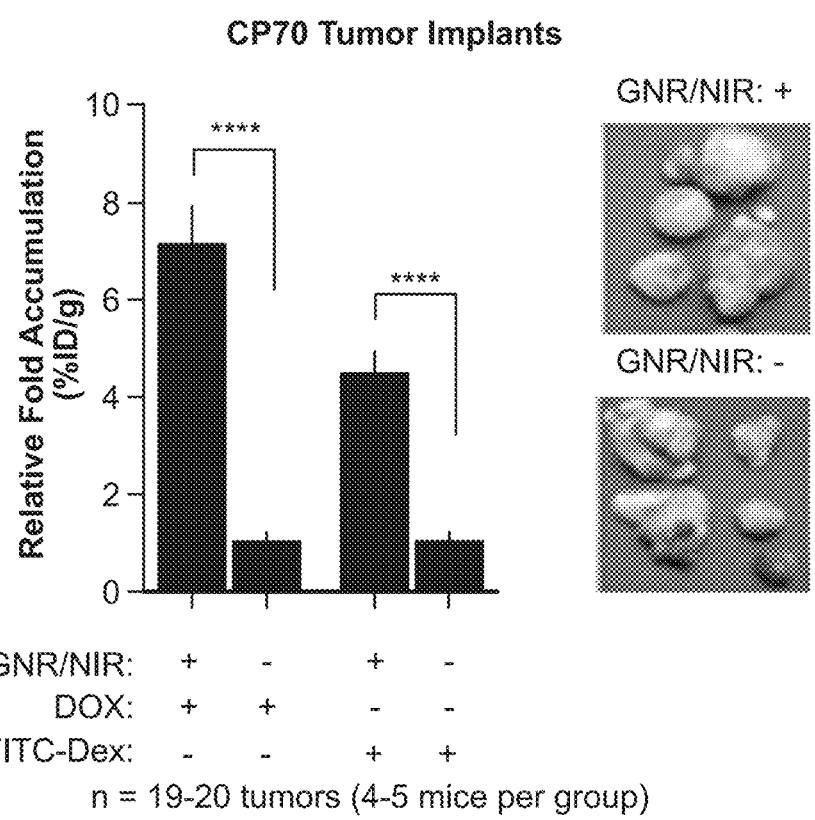

The IM-LD prototype illumination of the PEG-NRs reduced tumor size in a mouse model expressing CP70 human ovarian tumors. Once placed in the mice and connected to the power source, the IM-LDDs achieved the sub-ablative temperature range (40-45° C.) needed for PEG-NR therapy within 120 sec (2 min), as shown in FIG. 3A. PEG-NRs with NIR treatment increased the accumulation of doxorubicin in human CP70 ovarian tumor cells in the mouse model, and also increased uptake of FITC-labeled dextran, as shown in FIG. 3B. FITC-dextran is used to evaluate permeability and micro circulation in vivo. Tumors were smaller in mice treated with PEG-NRs/NIR than in mice treated without PEG-NRs/NIR. These preliminary studies confirm the feasibility of using the IM-LDD with PEG-NRs to potentiate tumor chemotherapy in an orthotopic ovarian cancer model.

Figure 4:
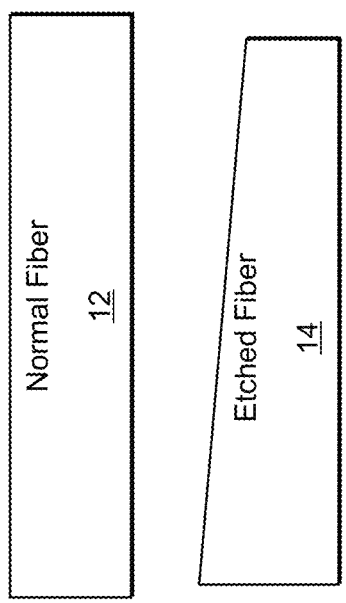
FIG. 4 is a schematic diagram illustrating laser cutter etching used in accordance with the invention.
Figure 5:
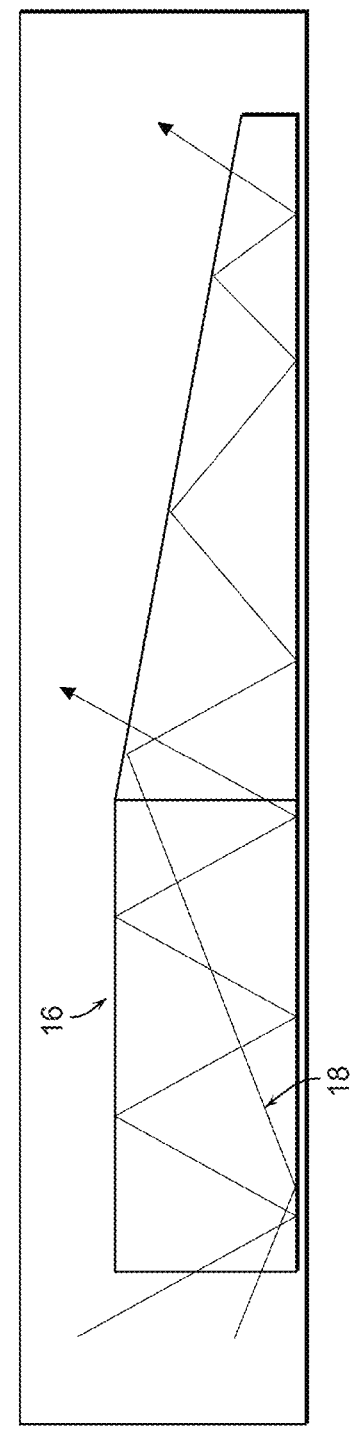
FIG. 5 is a schematic diagram illustrating a ray diagram of light rays propagating in an etched fiber.

To fabricate the invention a new process of light leakage was developed by etching a normal fiber 12 in a manner as seen in FIG. 4. The etch occurs in the cladding and can partially occur in the core of the normal fiber 12. The cut can be in one plane, multiple planes, or rotationally around the fiber. FIG. 5 shows an etched fiber 14 being etched on a single plane. This technique was used to develop the fiber structures of the IM-LDD.

Traditionally, in a fiber optic cable light travels down the fiber until the end of the fiber at which point it exits with some convergence or divergence pattern. With precision etching of the fiber, it allows for predictable illumination along the length of one fiber in a linear or non-linear controlled output. Due to the etching process, similarly aligned fibers will have similar etching and performance such that an array of fibers can be stacked in a one-dimension, two-dimensional, or three-dimensional pattern for predictable and uniform illumination.

TABLE 1

IM-LDD Specifications

| SPECIFICATION | MIN | MAX | METRIC |
|---|---|---|---|
| Illumination Wavelength | 250 | 2500 | nm |
| LDD Pad Width | 0.25 | 1000 | mm |
| LDD Pad Height | 1 | 1000 | mm |
| Bend Radius - Width | ∞ | 0.25 | mm |
| Bend Radius - Height | ∞ | 5 | cm |
| Accuracy | | | uW/$cm^2$ at each measurement point within +/−20% of the mean uW/$cm^2$ |
| Repeatability | | | uW/$cm^2$ at each measurement point within +/−10% of the median over 3 distinct measurements |
| Transmission Loss | — | 150 | dB/km |
| Tensile Strength | — | 50 | N |
| Coupling Configuration | | | Spherical Lens, Cylindrical Lens Coupling with Fiber Optic Input from Light Source or Butt-Coupling |
| Coupling Efficiency | 20% | 7.5% | Output uW/Input uW |
| Temperature Range | −55 | 70 | C. |
| Fiber - Plastic | | | Mitsubishi Rayon co., Ltd. Eska Polymer Optical Fiber |
| Sheath/Light Blocking | | | >90% |

Fibers could be etched by hand or non-motorized processes but the invention uses the precision and speed of a motorized laser cutter with the ability to cut in three-dimensions. The illumination output along the etching path will vary depending upon the depth of the cut (set by the power of the laser, focus of the laser, and the speed of the laser cut), the cut type (raster or vector), and the cut patterns (criss-cross, weave, etc) set in the laser cutter operation menu.

A ray of light 18 injected into a fiber optic cable 16 will bounce along off each core/cladding or core/air interface without otherwise changing its direction due to total internal reflection, as shown in FIG. 5. If however one core/cladding or core/air interface is angled with respect to the other (as in the etch) so that the fiber optic cable is shaped like a wedge, then each time the ray bounces off the angled core/cladding or core/air interface its direction will change with respect to the planar interface (bottom surface of the etched fiber 14 in FIG. 4 and the bottom surface of the ray diagram of the etched fiber 18 in FIG. 5). Repeated bounces will lead to the angle between the ray and the interface normal getting progressively smaller until the critical angle at which rays undergo total internal reflection is reached and the ray will then pass through the interface and emerge from the fiber optic cable. Varying light output patterns can be achieved by the linearity or non-linearity of the etch including periodic versus continuous etches.

The laser cutter is a laser on a 2D servo that allows for cuts to be made into materials by adjusting the laser's focal length, power, etching or cutting speed, the type of cut (raster or vector) or varying the cut pattern. The laser cutter is not new but the technique and patterns and the effect on the fiber is new. The ability to place the fiber in a rotational chuck within the laser cutter allows for cuts in three-dimensions, particularly rotational cuts allowing for complex cuts and illumination patterns.

The laser cutter is a laser on a 2D servo that allows for cuts to be made into materials by adjusting the laser's focal length, power, etching or cutting speed, the type of cut (raster or vector) or varying the cut pattern. The laser cutter is not new but the technique and patterns and the effect on the fiber is new. The ability to place the fiber in a rotational chuck within the laser cutter allows for cuts in three-dimensions, particularly rotational cuts allowing for complex cuts and illumination patterns.

This illumination effect from the etching process can occur on one fiber to make a single fiber illumination device which can be used for small surface areas on the body such as around noses, ears, or fingers. If multiple fibers are placed next to each other in the laser cutter, they can be uniformly cut and then with an adhesive can make a larger surface that can cover large surface areas of the body. Additionally, by stacking the fibers next to each other and then cutting a pattern into the fibers, these fibers can then be separated individually to make complex shapes providing even illumination. For example, the fibers can be arranged to make a stint that can be placed endoscopically in the body for treating esophageal cancer. Alternatively, the fibers can be arranged in a pattern around a mesh that could be implanted in the body around major organs/cavities to provide CLIPT/PDT illumination. For internal use of the LDD requires connecting the illumination source to the LDD externally, ideally through a sterile catheter.

The etch process can be performed on both glass and plastic fibers however plastic is preferred because of its ability to bend over tight bending radiuses without breaking or compromising irradiance over long CLIPT treatment sessions. Plus the plastic fiber is biocompatible and does not require strenuous sterilization for patient reuse. The specifications of the Plastic Fiber are provided in Table 2.

TABLE 2

| Mitsubishi SK-20 Property | Metric |
| --- | --- |
| Fiber Diameter | 0.550 mm |
| Fiber Core | 0.525 mm |
| Breaking Stress | 6 kg/fiber |
| Breaking Strain by Elongation | 100% |
| Transmission Loss | 150 db/km |
| Temperature Range | −55~+70 C. |
| Cored Refractive Index | 1.49 |
| Cladding Refractive Index | 1.39~1.42 |
| Accept Angle | 60 deg |
| Bending Radius | 2 dB at 5 mm/0.5 dB at 20 mm |
| Flammability | NA |

To provide additional light directionality from the fiber, a diffuser, ideally an off the shelf diffuser, can be placed over one or more fibers. The diffuser can help change the light behavior of one or more fibers particularly in conjunction with the etching process. For even illumination along the length of the fiber, the typical configuration for Roger Scientific Inc.'s IM-LDDs, the etch of the fiber will be made in such a way that the illumination exiting from the entire length of the fiber is constant.

This fiber optic etching approach to precision and uniform light delivery allows less fiber to be consumed compared to the Lumitex approach and it also makes the device thinner because the etch can be used on the thinnest fibers in the market. Also, with only a single 1-D array of fibers the IM-LDD becomes flexible allowing it to curve naturally to the anatomical features of the body compared to the rigid Lumitex device. This makes it possible to curve the IM-LDD to cavities and luminal surface or other very small anatomical areas with radius of curvatures up to 0.25 mm.

Another approach to etching the fibers with the laser cutter is to use mechanical means to adjust the etching process rather than using the laser cutter settings. A mechanical fixture with an inclined ramp can be used to hold the fibers of the LDD in the laser cutter at various focal lengths of the laser. Various focal lengths will provide variation in the power which affects the depth of the laser cut along the fiber, thus creating an etched ramp along the length of the fiber. Depending on the ramp angle, the cut depth and light diffusion of one or more fiber optic cables can be changed. The mechanical ramp fixture is made of aluminum and is capable of holding or more fibers, however, in this fixture, only a one dimensional cut is allowed.

Figure 6:
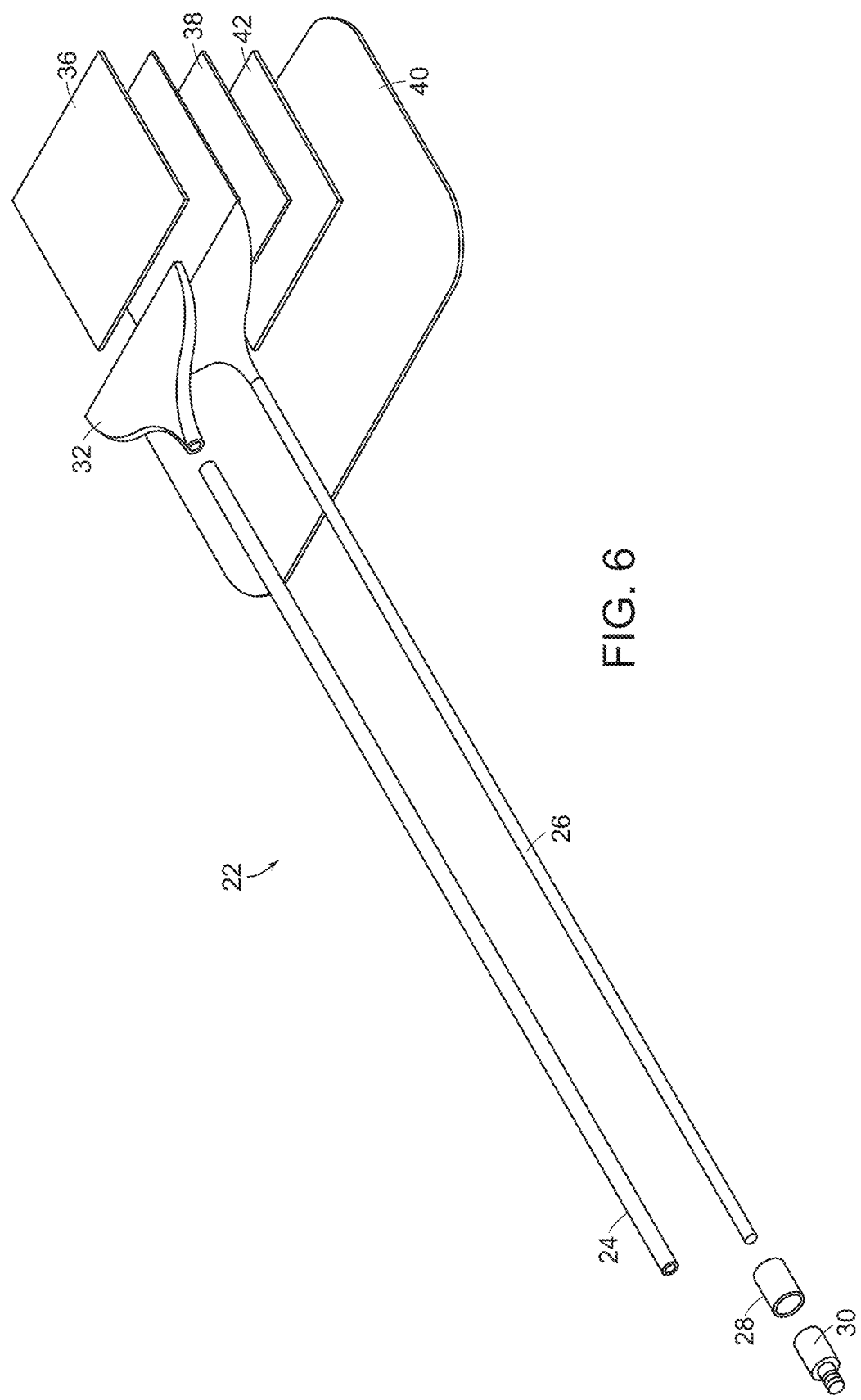
FIG. 6 is a schematic diagram illustrating light source of the IM-LDD used in accordance with the invention.

FIG. 6 shows the inventive IM-LDD 22 used in accordance with the invention. The IM-LDD includes a first rod assembly 24 and a second rod assembly 26. The first rod assembly 24 defines a silicon house used to house the second rod assembly 26 that defines a fiber bundle. A fiber bundle 26 includes a plurality of individual fibers bundled together. One end of the first rod assembly is connected to an optical coupler 28. The optical coupler 28 is connected to a lens assembly 30. On the other end of the first rod assembly 28 is connected to a fiber transition module 32. The fiber transition module 32 is connected to pad structure 34 that includes a white foam layers 36 and 42, a polyester layer 38, and adhesive layer 40.

Once fabrication is completed the IM-LDD pad fibers require adhesion to maintain rigidity, optical clarity, flexibility, and alignment. The adhesive layer 38 is off-the shelf and can include adhesives to varying fabrics, garments, or structures. Once the IM-LDD pad 34 is assembled and into a fixed pattern the proximal end needs to be coupled to the illumination source (currently a laser) by the optical coupler 28. The optical coupler 28 can direct the light into the LDD by focusing the illumination in a line array using the cylindrical lens assembly 30 or the LDD can collimate a circular beam into a circularly composed array of fibers.

Figure 7:
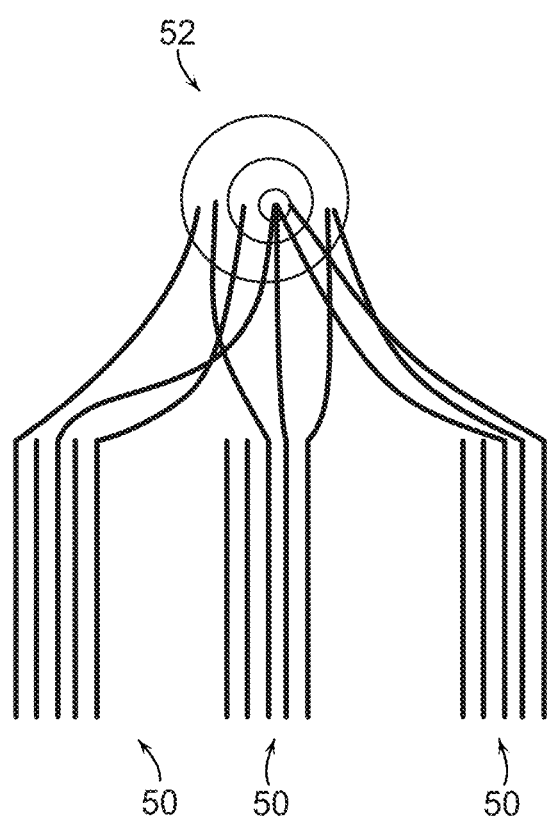
FIG. 7 is a schematic diagram illustrating non uniform placement of light delivery device (LDD) to Gaussian beam.

The fibers 50 can be held in a circular array mount at the proximal end by means of a mechanical ring 52 as shown in FIG. 7. Placement of the fibers 50 is not critical if the beam uniformity from the coupler is uniform. If the beam uniformity is not uniform or Gaussian, if the illumination source is Gaussian, then the fibers 50 from different regions of the IM-LDD pad can be placed in different regions of the IM-LDD mechanical holding ring 52 as seen in FIG. 7. By placing the fibers 50 in precise locations along a non-uniform beam, allows the user to dissipated hot spots by increasing or decreasing the irradiance at the pad.

Another approach for coupling illumination into the IM-LDD in which no bulky glass or plastic optics are used. Rather, since the IM-LDD circular bundle can be 0.5 cm in diameter, it can be fed to match the diameter of the SMA fiber Numerical Aperture output. However, this approach will have coupling efficiency loss as the SMA output is diverging and will have different coupling effects for fibers on axis versus those fibers on the perimeter of the coupling ring 28 as shown in FIG. 7.

The alternative coupling housing can be made of Rydell or PEK, a very light weight and biocompatible plastic material. This reduces the weight drag attached to the LDD, which is important when a human subject is wearing the LDD in critical sites. Lowering the weight also makes the LDD more comfortable to wear over the extended CLIPT treatment.

In addition to the IM-LDD design and fabrication described above, there are alternative embodiments of the IM-LDD device and system.

The IM-LDDs described have been fabricated using plastic or glass fiberoptic materials. Additional techniques could be used to develop IM-LDDs with silk, specifically spider silk. It has similar optical properties as fiber optics for illumination in luminal cavities. More importantly, spider silk is biocompatible and will biologically dissolve over time. Hence, a silk based IM-LDD could naturally dissolve rather than require surgery to remove the IM-LDD after one or more months of chronic treatments.

Figure 8:
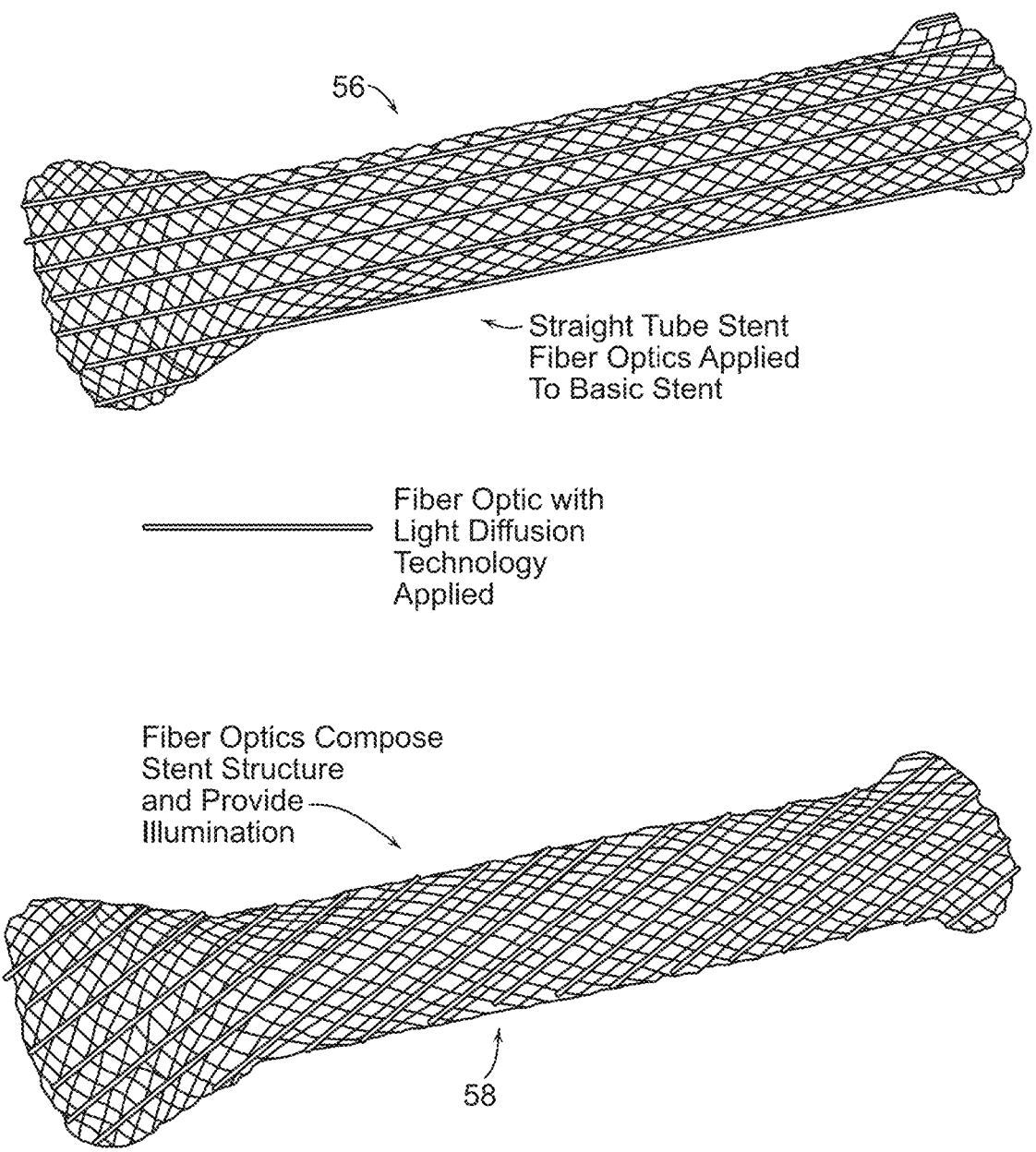
FIG. 8 is schematic diagram illustrating stent structures composed of fibers used in accordance with the invention.

Another feature is that due to the flexibility of the Light Diffusion Technology (LDT) process, single fibers can be treated and woven into fabrics that can be shaped in circular patterns such as a stent. Additionally, the stent can be made directly from the fibers in a square IM-LDD format rolled into a circular stent. A light illuminating stent could be used for esophageal PDT. An example of a cylindrical stents 56, 58 with single fiber woven into fabrics are attached to an existing stent or composed into an array to make a stent structure for the esophagus is shown in FIG. 8.

To make the IM-LDD portable for at-home or chronic care, the illumination device generating the light going into the IM-LDD must be portable. To do this, RSI has developed the portable light device (PLD) which includes a light emitting diode (LED) source, a power source to power the LED, and controller electronics to control light output from the LED based on the battery input. The controller electronics also control additional user defined features to control the treatment time, power output, and provides thermal and electrical safety monitoring.

Although one could use any light source that can match the wavelength activation spectrum of the light-activated cancer therapy, one can chose to use inexpensive, compact, and cooled light emitting diodes as opposed to a laser or laser diode. Although one could use various forms of LEDs such as organic LEDs (OLEDs), the standard, high lumen/watt efficient LEDs were chosen. One can develop a red 630 nm 16-die 0-5 W LED PLD and a 808 nmm NIR 7-die 2 W LED PLD. The wavelength output can be modified to work at other wavelengths by using the appropriate LED. The PLD meets the specifications of Table 3. The PLD is compact and can be strapped to a human subject by means of a belt clip or in a fanny pack.

The PLD uses two techniques to reduce heat over traditional LED illumination devices. One method uses a coolant gel at the board level allowing for reduced heat buildup at circuit connections. The second method uses a light and compact heat sink fan on the back side of the LED module.

TABLE 3

Rogers Sciences LED PLD SPECIFICATIONS

| LED PLD SPECIFICATIONS | MIN | MAX | METRIC |
|---|---|---|---|
| Wavelength | 250 | 2500 | (nm) Light-Activated Therapy Specific |
| Irradiance | 0.050 | 10000 | mW/cm² |

TABLE 3-continued

Rogers Sciences LED PLD SPECIFICATIONS

| LED PLD SPECIFICATIONS | MIN | MAX | METRIC |
|---|---|---|---|
| Dimensions | — | <10 | cm³ |
| Weight | — | <5 | Kg |
| Optical Coupling | Fiber Optic | | |
| LED Mounting | Surface Mounted | | |
| Cooling | Heat Sink and Fan and Cooling Gel | | |

Figure 9:
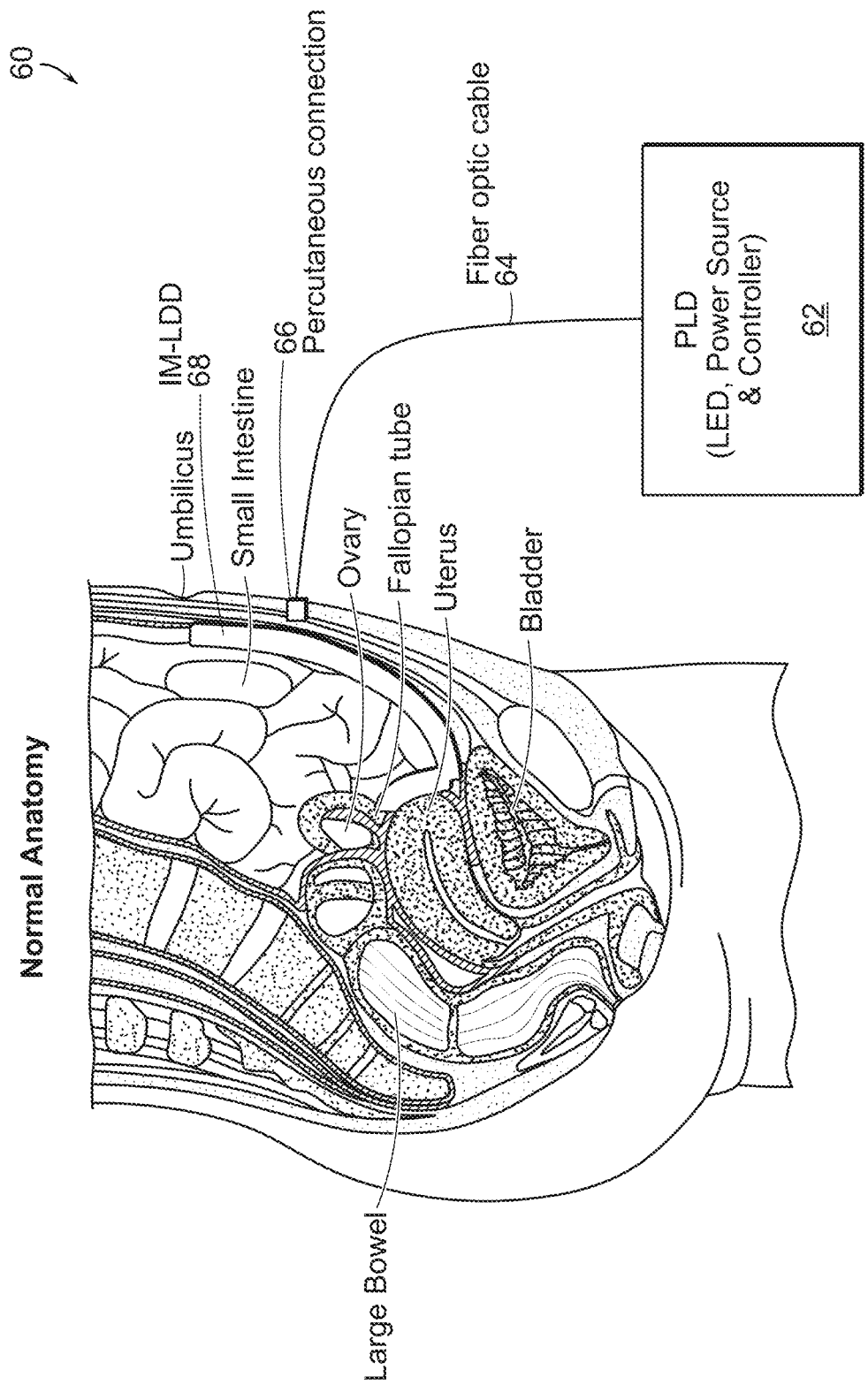
FIG. 9 is schematic diagram illustrating a percutaneous connection of the IM-LDD to the PLD and energy source.
Figure 10:
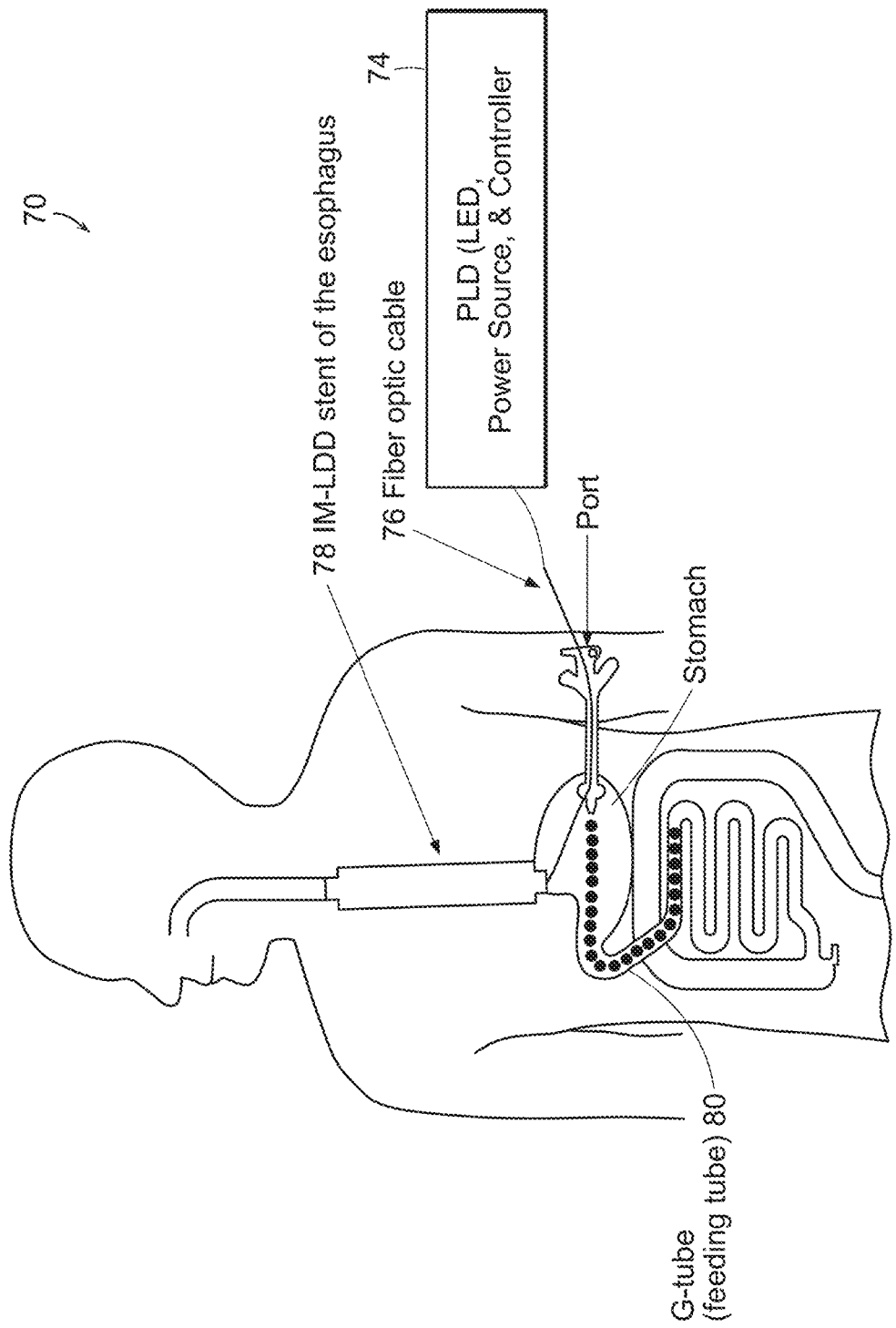
FIG. 10 is schematic diagram illustrating a percutaneous connection for an IM-LDD implanted into the esophagus as a stent.

For internal use of the IM-LDD requires connecting the PLD LED illumination source to the IM-LDD externally. There are 3 primary options for powering the IM-LDD whether fabricated as a cylinder (stent for a luminal surface) or planar (for body cavity lining):

FIG. 9 shows a show system 60 having a PLD 62 (includes LED, power source, and controller electronics) outside the body and percutaneously connect 66 the IM-LDD 68 and PLD 62 through a fiberoptic cable 64. This is the preferred embodiment for the IM-LDD as an esophageal stent, biliary stent and for use in the bladder, prostate, and ureter. FIG. 10 shows a system 70 under this configuration of an implantable stent in the luminal surface of the esophagus where the stent receives light from the PLD 74 via a fiber optic cable 76, passing thru a port 82, in a multi-channel G-tube 80. The G-tube 80 is used to help the patient receive food and fluids. The fiber optic cable attaches to the IM-LDD 78.

As one alternative embodiment, the PLD could be composed of one or more light sources (LED, laser diode, or laser) and a power controller which are also connected to the IM-LDD and implanted. The PLD will receive power from an external power source via a thin cable.

An additional alternative embodiment is to have one or more miniaturized light sources, such as LEDs weaved into a fabric which would act as an IM-LDD which could be implanted. The miniaturized light sources could be powered by an external power cable.

Figure 11:
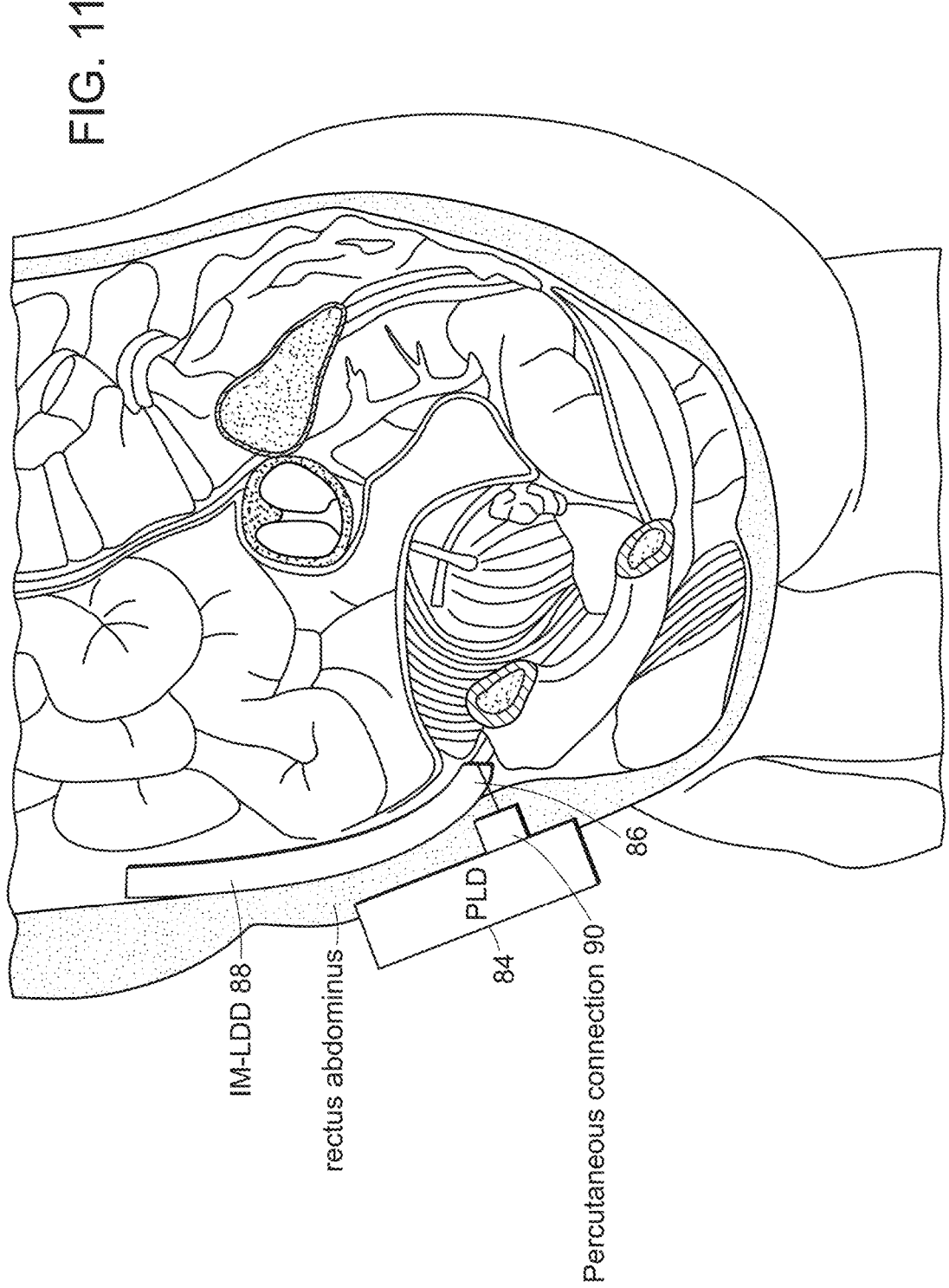
FIG. 11 is schematic diagram illustrating the invention being applied for lower-abdominal treatments.

For lower-abdominal treatments, place the power supply and PLD (includes LED) 84 outside the body, with the PLD LED 84 subcutaneously positioned on rectus abdominus or pectoralis major muscle. The large muscle group acts as a thermal sink for the heat emitted from the LED. A fiber-optic cable 86 passes light from the PLD LED to the IM-LDD 88 on the target tissue thru the percutaneous connection 90 as shown in FIG. 11.

Figure 12:
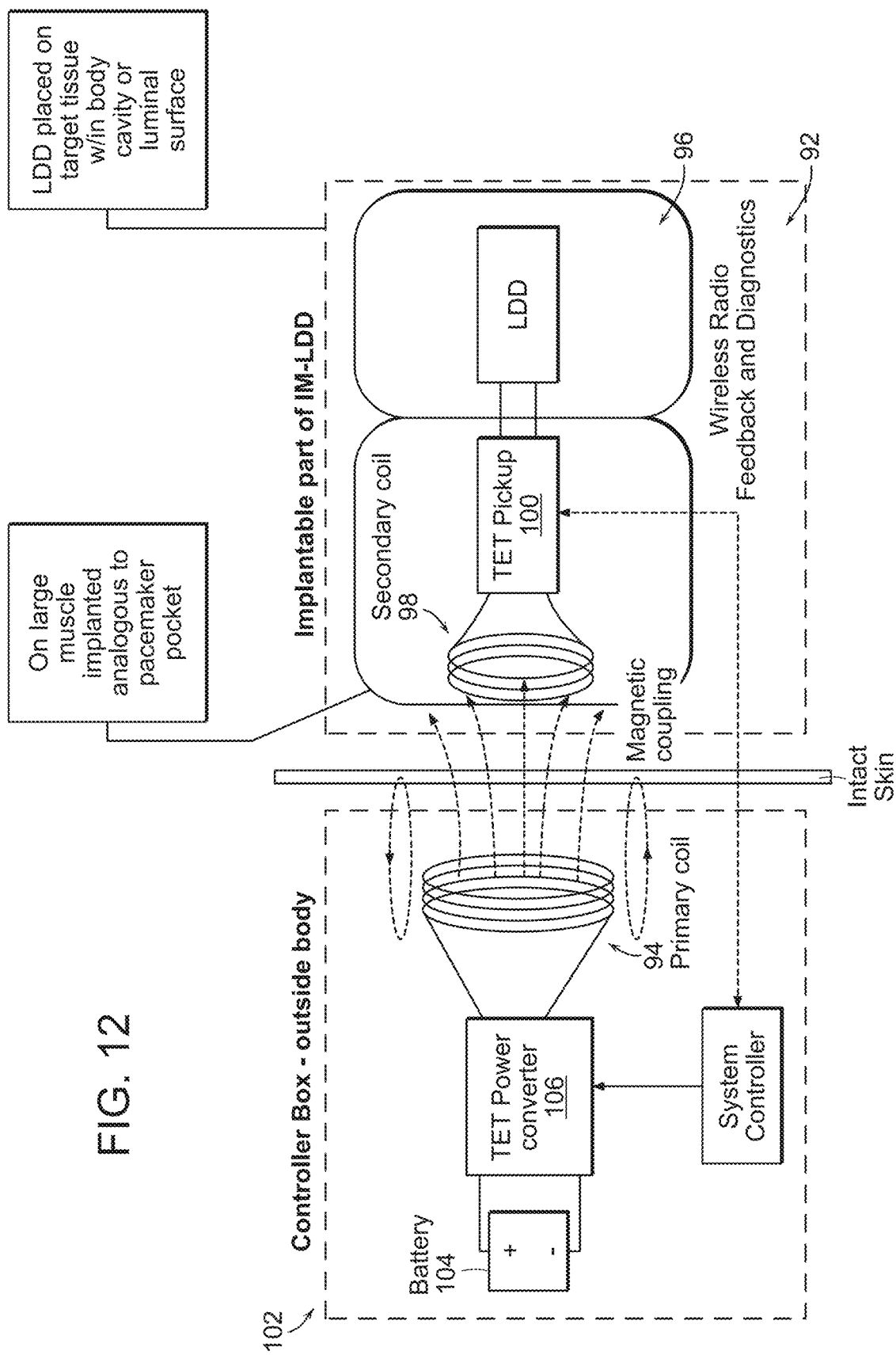
FIG. 12 is schematic diagram illustrating an embodiment of the invention.

The entire system is implanted. An RF-coil 98 is packaged with the PLD (LED, power, and controller electronics) 96 and is placed on a large muscle group subcutaneously. The internal RF-coil 98 and PLD 96 are powered via an external system 102 having a wearable Transcutaneous Energy Transfer (TET) system 104 coupled to a RF coil 94 shown in FIG. 12. The external system 102 can be powered by either rechargeable batteries 104 or another power source. These external power systems are currently being used for a number of cardiac assist devices.

The implantable system 100 includes of an external system 102 that the patient wears, that powers, controls and monitors the implanted system 100, and an implanted system 92, which includes the PLD 96 and an internal TET device 100. In addition, the implantable system 100 a rechargeable battery capable of running a limited number of PDT treatments before being recharged from the external system.

The internal components can be implanted surgically via a single minimally invasive surgical procedure, or at the time of definitive surgical management of the tumor. The controller and LED or possibly laser, housed in a single PLD implanted module 96 approximately the size of an implanted defibrillator (a deck of cards), can be implanted between the skin and the fascia in the lower abdomen. This module will be connected to an internal TET receiver 100, which provides the internal system power. The TET receiver 100 can either be integrated with the PLD 96 or separate and connected with a hermetic cable. The PLD 96 can also have fiber-optic outputs to delivery energy to the IM-LDD in the treatment zone.

Under normal conditions, the patient will be dosed with the desired PDT drug. The dosages will depend on the weight of the patient and the expected clearance rate of the patient. At a predetermined time, the LED or laser illumination will be activated for PDT. During this time the patient will wear the external TET 106 to power and monitor the therapy. This can be completed at any location, since the external system is highly portable. After the desired exposure time, the patient will be un-tethered from the external system. The patient's clinical progress can be monitored using the usual non-invasive monitoring (preferably CT scan) and the PDT sessions can be adjusted accordingly.

The efficacy of the proposed implanted devices and light delivery will be highly dependent upon the timing between drug delivery and light exposure. Software can maximize tumor kill and minimize toxicity by varying wavelength, fluence, duration and timing of light delivery and dose and timing of drug delivery. This will be calculated on a per patient basis.

The IM-LDD can be used for applications with drugs, particularly therapeutic cancer drugs, and without drugs. Initial treatment applications surrounding the field of photodynamic therapy that could use the IM-LDD include: (1) Initial Targets: Treatment of metastatic (peritoneal implants) or unresectable malignancies of the peritoneal cavity will be targeted. This will include primarily metastatic colon cancer, pancreatic cancer, ovarian and endometrial malignancies. All these tumors have shown some clinical response to PDT; (2) Secondary Targets: Adjuvant treatment (PDT in conjunction with surgery, radiotherapy, chemotherapy) of primary abdominal and pelvic tumors. Duke C colon cancer, endometrial and ovarian cancer, with PDT implantation at time of primary resection; (3) Future Targets: In addition to solid tumors, other chronic diseases could be targeted by strategic implantation of the light source and selection of targeting drug. For example, chronic infections which are resistant to antibiotics, chronic tuberculosis and abscess pockets, may be amenable to PDT given over multiple sessions over months.

Additionally, an IM-LDD platform with CLIPT could be used as a treatment for atherosclerotic cardiovascular diseases by using the light from the IM-LDD along with drugs to target calcium (tagging photosensitizers to chelators), cholesterol (tagging to a highly lipophillic moity), and compounds present in vulnerable plaques in arteries. The IM-LDD composed of fiber optics delivery light or miniaturized light sources (such as one or more LEDs, laser diodes, or lasers) could be implanted onto the myocardial surface could, in conjunction with a targeted drug therapy such as CLIPT over months/years, slowly dissolve plaques and avoiding issues of re-stenosis. This would provide a viable alternative to coronary artery bypass grafting (CABG) and angioplasty/stent placement.

Additionally, the IM-LDD could be used for applications ranging in low energy illumination for accelerated wound healing, traumatic brain injury, and spinal chord injury as adjuvant to facilitate repair. Moreover, the invention operates in the UV range providing numerous potential applications for treating infections and inflammatory diseases, from pneumonia to endometriosis, with light alone or via PDT. This includes many applications in the wound healing, microbe-killing and anti-inflammatory space.

Although the present invention has been shown and described with respect to several preferred embodiments thereof, various changes, omissions and additions to the form and detail thereof, may be made therein, without departing from the spirit and scope of the invention.

What is claimed is:

1. An implantable light delivery device (IM-LDD) comprising a light source that can emit illumination and be implanted within body cavities or luminal surfaces enabling energy at one or more wavelengths to reach and provide therapy treatment at selected region, the light source comprises etched optical fibers having a plurality of rigid and flexible shapes that emit a specific illumination within the body cavities or luminal surfaces for a period of time.

2. The IM-LDD of claim 1, wherein the body cavities or luminal surfaces comprise esophagus, upper and lower GI tract, genito-urinary tract, bladder, pelvis, peritoneum, pulmonary cavity, hepatobilliary tree, bronchial tree, blood vessels or calvarium/CNS.

3. The IM-LDD of claim 1, wherein the light source provides repeated, continuous or recurrent light delivery.

4. The IM-LDD of claim 1, wherein the light source comprises an optical element array delivering the required therapeutic doses.

5. The IM-LDD of claim 4, wherein the therapeutic doses comprise NIR energy for PEG-NR activation.

6. The IM-LDD of claim 1, wherein light source comprises fibers rolled into a circular stent.

7. The IM-LDD of claim 1, wherein the light source comprises a pad structure coupled to optical fibers to be implanted.

8. The IM-LDD of claim 1, wherein the light source comprises an internal RF-coil and an internal control mechanism being powered via an external system.

9. The IM-LDD of claim 8, wherein the external system comprises a wearable Transcutaneous Energy Transfer (TET) system coupled to a second RF coil.

10. The IM-LDD of claim 1, wherein the therapy treatment comprises Photodynamic therapy (PDT) or Photo Thermal Therapy (PTT).

11. A light-based therapy device comprising:
   a controller mechanism that produces power and control signals to enable operation of one or more medical devices; and
   an implantable light delivery device (IM-LDD) that is coupled to the controller mechanism that receives the power and the control signals to enable a light source to emit illumination, the light source is implanted within body cavities enabling energy at one or more wavelengths to reach and provide therapy treatment to a selected region, the light source comprises etched optical fibers having a plurality of rigid and flexible shapes that emit a specific illumination within the body cavities or luminal surfaces.

12. The light-based therapy device of claim 11, wherein the body cavities or luminal surfaces comprise esophagus, upper and lower GI tract, genito-urinary tract, bladder, pelvis, peritoneum, pulmonary cavity, hepatobilliary tree, bronchial tree, blood vessels or calvarium/CNS.

13. The light-based therapy device of claim 11, wherein the light source provides repeated, continuous, or recurrent light delivery.

14. The light-based therapy device of claim 11, wherein the light source comprises an optical element array delivering the required therapeutic doses.

15. The light-based therapy device of claim 14, wherein the therapeutic doses comprise NIR energy for PEG-NR activation.

16. The light-based therapy device of claim 11, wherein light source comprises fibers rolled into a circular stent.

17. The light-based therapy device of claim 11, wherein the light source comprises a pad structure coupled to optical fibers to be implanted.

18. The light-based therapy device of claim 11 wherein the light source comprises an internal RF-coil and an internal control mechanism.

19. The light-based therapy device of claim 18, wherein the control mechanism comprises a wearable Transcutaneous Energy Transfer (TET) system coupled to a second RF coil.

20. The light-based therapy device of claim 11, wherein the therapy treatment comprises Photodynamic therapy (PDT), Photo Thermal Therapy (PTT), or a combination of PDT and PTT.

21. A method of performing light-based therapy treatment comprising:
 providing a controller mechanism that produces power and control signals to enable operation of one or more medical devices; and
 providing an implantable light delivery device (IM-LDD) that is coupled to the controller mechanism that receives the power and the control signals to enable a light source to emit illumination; and
 implanting the light source within body cavities enabling energy at one or more wavelengths to reach and provide photodynamic therapy (PDT) treatment to a selected region, the light source comprises etched optical fibers having a plurality of rigid and flexible shapes that emit a specific illumination within the body cavities or luminal surfaces.

22. The method of claim 21, wherein the body cavities or luminal surfaces comprise esophagus, upper and lower GI tract, genito-urinary tract, bladder, pelvis, peritoneum, pulmonary cavity, hepatobilliary tree, bronchial tree, blood vessels or calvarium/CNS.

23. The method of claim 21, wherein the light source provides repeated, continuous, or recurrent light delivery.

24. The method of claim 21, wherein the light source comprises an optical element array delivering the required therapeutic doses.

25. The method of claim 24, wherein the therapeutic doses comprise NIR energy for PEG-NR activation.

26. The method of claim 21, wherein light source comprises fibers rolled into a circular stent.

27. The method of claim 21, wherein the light source comprises a pad structure coupled to optical fibers to be implanted.

28. The method of claim 21 wherein the light source comprises an internal RF-coil and an internal control mechanism.

29. The method of claim 28, wherein the control mechanism comprises a wearable Transcutaneous Energy Transfer (TET) system coupled to a second RF coil.

30. The method of claim 21, wherein the therapy treatment comprises Photodynamic therapy (PDT), Photo Thermal Therapy (PTT), or a combination of PDT and PTT.

* * * * *